(12) United States Patent
Chevreau

(10) Patent No.: US 9,289,374 B2
(45) Date of Patent: Mar. 22, 2016

(54) TOPICAL COMPOSITIONS AND METHODS FOR REDUCING OXIDATIVE STRESS

(71) Applicant: LifeVantage Corporation, Sandy, UT (US)

(72) Inventor: Nathalie Chevreau, Salt Lake City, UT (US)

(73) Assignee: LifeVantage Corporation, Sandy, UT (US)

( * ) Notice: Subject to any disclaimer, the term of this patent is extended or adjusted under 35 U.S.C. 154(b) by 0 days.

(21) Appl. No.: 14/260,149

(22) Filed: Apr. 23, 2014

(65) Prior Publication Data

US 2015/0306022 A1 Oct. 29, 2015

(51) Int. Cl.
| | |
|---|---|
| *A01N 65/00* | (2009.01) |
| *A61K 8/97* | (2006.01) |
| *A61K 8/35* | (2006.01) |
| *A61K 8/41* | (2006.01) |
| *A61K 8/46* | (2006.01) |
| *A61K 8/49* | (2006.01) |
| *A61K 8/60* | (2006.01) |
| *A61Q 19/00* | (2006.01) |
| *A61Q 19/08* | (2006.01) |

(52) U.S. Cl.
CPC ... *A61K 8/97* (2013.01); *A61K 8/35* (2013.01); *A61K 8/41* (2013.01); *A61K 8/46* (2013.01); *A61K 8/494* (2013.01); *A61K 8/60* (2013.01); *A61Q 19/00* (2013.01); *A61Q 19/08* (2013.01)

(58) Field of Classification Search
CPC .................................................. A61K 36/00
USPC ......................................................... 424/725
See application file for complete search history.

(56) References Cited

U.S. PATENT DOCUMENTS

| 7,939,115 B2 | 5/2011 | Huang et al. |
| 2007/0196318 A1 | 8/2007 | Marini |
| 2008/0146987 A1 | 6/2008 | Soumyanath et al. |
| 2013/0338039 A1 | 12/2013 | Mazed et al. |

FOREIGN PATENT DOCUMENTS

| WO | 2005/094862 A1 | 10/2005 |
| WO | 2010/127912 A1 | 11/2010 |
| WO | 2011/097572 A1 | 8/2011 |
| WO | 2012/009298 A2 | 1/2012 |
| WO | 2012/068454 A2 | 5/2012 |
| WO | 2012/142511 A2 | 10/2012 |
| WO | 2013/049507 A1 | 4/2013 |

OTHER PUBLICATIONS

United States Patent and Trademark Office, acting as the International Searching Authority, "International Search Report and Written Opinion," mailed Jul. 20, 2015 in International Patent Application No. PCT/US2015/027094.

*Primary Examiner* — Michael Meller
(74) *Attorney, Agent, or Firm* — Stoel Rives LLP

(57) ABSTRACT

A composition for the topical application on a mammalian skin comprises one or more *Brassica* plant extracts selected from the group consisting of: *Brassica juncea* extract, *Brassica oleracea italica* extract, *Brassica oleracea capitata* extract, *Brassica oleracea botrytis* extract, and *Brassica oleracea acephala* extract. The composition further comprises one or more selected from the group consisting of: *Curcuma longa* extract, curcuminoids, tetrahydrocurcuminoids, metabolites of curcuminoids or tetrahydrocurcuminoids, and derivatives of curcuminoids or tetrahydrocurcuminoids. The composition further comprises one or more selected from the group consisting of: *Camellia oleifera* extract, *Camellia sinensis* extract, green tea extract and white tea extract; *Wasabia japonica* extract; *Bacopa monnieri* extract; *Silybum marianum* extract; and one or both of *Piper nigrum* extract or tetrahydropiperine.

7 Claims, 2 Drawing Sheets

TOPICAL COMPOSITIONS AND METHODS FOR REDUCING OXIDATIVE STRESS

FIELD OF THE INVENTION

This invention generally relates to skin care compositions and, more particularly, to topical compositions and methods for reducing oxidative stress in a skin of a mammalian subject.

BACKGROUND

One of the major causes of skin aging is oxidative stress. Oxidative stress is associated with increased production of reactive oxygen species, such as free radicals and peroxides, or a significant decrease in the effectiveness of the body's antioxidant defenses. When left untreated, oxidative stress may cause skin to exhibit wrinkles, uneven skin tone, loss of skin thickness and elasticity, and other signs of skin aging. Oxidative stress may also cause double-stranded DNA breaks, which are among the more serious types of DNA damage.

Despite great demand, many anti-aging skin care products and treatments have not been proven to demonstrate the desired positive effects. Even the best performing creams often provide only slight, short-term improvement in the skin's appearance. A great diversity of active ingredients and combinations thereof may be found in the anti-aging creams currently on the market. While many of the active ingredients suspected of providing a beneficial, anti-aging effect on skin may be known, the optimal combination of these and other ingredients that provide a synergistic anti-aging effect remains unknown.

BRIEF SUMMARY

Compositions are described herein, preferably for topical application on a skin, hair, nails or other external surface of a mammalian subject. The compositions are believed to stimulate the cutaneous intrinsic defense mechanisms to improve the appearance and overall health of the skin. Topical application of the compositions has been demonstrated to stimulate some Nfr2 target genes to reduce oxidative stress. Specifically the expression of catalase is highly expressed which is a key antioxidant enzyme in the body's defense against oxidative stress. The topical application of the compositions also stimulates a DNA repair response which contributes to maintain homeostasis between cellular apoptosis and hyperproliferation. Topical administration of the compositions has also been demonstrated to improve the appearance of skin by increasing the skin's thickness, increasing the relief of the epidermal rete ridges and/or increasing the density of the collagen network in the dermis. The compositions may be provided in a variety of forms suitable for topical application, such as cosmetics, pharmaceutical compositions, sunscreen, lotions, creams, serums, skin lotions, and cleansers. The compositions may also be provided in a kit comprising a cleanser, a lotion, an eye serum and an anti-aging cream.

In one embodiment, compositions for topical application on a skin of a mammalian subject are described. The compositions may comprise one or more *Brassica* plant extracts selected from the group consisting of: *Brassica juncea* extract, *Brassica oleracea italica* extract, *Brassica oleracea capitata* extract, *Brassica oleracea botrytis* extract, and *Brassica oleracea acephala* extract. The compositions may further comprise one or more selected from the group consisting of: *Curcuma longa* extract, curcuminoids, tetrahydrocurcuminoids, metabolites of curcuminoids or tetrahydrocurcuminoids, and derivatives of curcuminoids or tetrahydrocurcuminoids. The compositions may further comprise one or more selected from the group consisting of: *Camellia oleifera* extract, *Camellia sinensis* extract, green tea extract, and white tea extract. The compositions may further comprise *Wasabia japonica* extract, *Bacopa monnieri* extract, *Silybum marianum* extract, and one or both of *Piper nigrum* extract or tetrahydropiperine.

In accordance with a first aspect, the one or more *Brassica* plant extracts comprises *Brassica juncea* extract, *Brassica oleracea italica* extract, *Brassica oleracea capitata* extract, *Brassica oleracea botrytis* extract, and *Brassica oleracea acephala* extract.

In accordance with a second aspect, the composition further comprises *Plantago lanceolata* extract.

In accordance with a third aspect, the derivatives of tetrahydrocurcuminoids is one or more selected from the group consisting of: tetrahydrodiferuloylmethane, tetrahydrodemethoxydiferuloylmethane and tetrahydrobisdemethoxydiferuloylmethane.

In accordance with a fourth aspect, the *Bacopa Monnieri* extract, the *Silybum marianum* extract, the tetrahydropiperine, and the tetrahydrocurcuminoids is present in the composition in an amount ratio of at least 2:2:1:1, respectively.

In another embodiment, compositions for topical application on a skin of a mammalian subject are described. The compositions may comprise one or more selected from the group consisting of: *Curcuma longa* extract, curcuminoids, tetrahydrocurcuminoids, and metabolites and/or derivatives of curcuminoids and/or tetrahydrocurcuminoids. The compositions may further comprise one or more selected from the group consisting of: *Camellia oleifera* extract, *Camellia sinensis* extract, green tea extract, and white tea extract. The compositions may further comprise *Bacopa monnieri* extract, *Silybum marianum* extract and one or both of *Piper nigrum* extract or tetrahydropiperine.

In accordance with a first aspect, the *Bacopa monnieri*, the *Silybum marianum*, white tea extract, the tetrahydropiperine, and the *Curcuma longa* extract are present in the composition in an amount ratio of at least 4:4:4:1:1, respectively.

In accordance with a second aspect, the *Bacopa monnieri*, the *Silybum marianum*, white tea extract, the tetrahydropiperine, and the *Curcuma longa* extract are present in the composition in an amount ratio of at least 7:7:7:2:1, respectively.

In a further embodiment, compositions for topical application on a skin of a mammalian subject are described. The compositions may comprise one or more isothiocyanates, one or more selected from the group consisting of: *Curcuma longa* extract, curcuminoids, tetrahydrocurcuminoids, metabolites of curcuminoids or tetrahydrocurcuminoids, and derivatives of curcuminoids or tetrahydrocurcuminoid, one or more phenylpropanoids, and tetrahydropiperine.

In accordance with a first aspect, the one or more isothiocyanates is present in the composition in an amount of 500-1,500 ppm.

In accordance with a second aspect, the one or more isothiocyanates comprises sulforaphane.

In accordance with a third aspect, the one or more phenylpropanoids is plantamajoside. The plantamajoside may be present in the composition in an amount of 100 to 2,500 ppm, preferably 250 to 2,000 ppm, and most preferably 500 to 1,500 ppm.

In accordance with a third aspect, the compositions further comprise one or more selected from the group consisting of: *Camellia oleifera* extract, *Camellia sinensis* extract, green tea extract, and white tea extract.

In accordance with a fourth aspect, the compositions further comprise one or more bacosides. Preferably, the one or more bacosides comprise bacoside A.

In accordance with a fifth aspect, the compositions further comprise one or more flavonolignans. Preferably, the flavonolignans are one or more selected from the group consisting of silymarin, silibinin, silychristin, silydianin, dehydrosilybin, deoxysilycistin, deoxysilydianin, silandrin, silybinome, silyhermin, and neosilyhermin.

In accordance with a sixth aspect, the compositions further comprise tetrahydropiperine.

In yet a further embodiment, methods of treating the skin of a mammalian subject are described. The methods may comprise applying any one of the above-described compositions to the skin of the mammalian subject in an amount effective to stimulate cutaneous intrinsic defense in the subject.

In accordance with a first aspect, the cutaneous intrinsic defense is controlling transcription of the Nuclear factor erythroid 2-related factor 2 (Nrf2) target genes and Nrf2-regulated pathways to restore or maintain a desired cellular redox balance in the mammalian subject.

In accordance with a second aspect, the cutaneous intrinsic defense is up-regulating the Nrf2 target genes.

The Nrf2 target genes may be one or more selected from the group consisting of: catalase (CAT), activating transcription factor 3 (ATF3) and peroxiredoxin 3 (PRDX3) genes.

In accordance with a third aspect, the cutaneous defense is restoring or maintaining a desired endogenous Nrf2 cellular level in the mammalian subject.

In accordance with a fourth aspect, the cutaneous defense is regulating Nrf2 activity by cytoplasmic phosphorylation of Nrf2 through phosphotidylinositol 3-kinase catalytic subunit alpha (PIK3CA) and by formation of a nuclear complex Nrf2-prothymosin, alpha (PTMA) that prevents permanent induction of Nrf2-regulated genes.

In accordance with a fifth aspect, the cutaneous defense is increasing an amount and activity of catalase in the mammalian subject.

In accordance with a sixth aspect, the cutaneous defense is maintaining the balance between epidermal cell apoptosis and epidermal cell hyperproliferation.

In accordance with a seventh aspect, the cutaneous defense is inhibiting the production of thymine dimers after exposure to UV-A and UV-B radiation.

In accordance with an eighth aspect, the cutaneous defense is repairing DNA double strand breaks and modulating cell cycle progression to permit DNA repair. The repairing and modulating may be triggered by the up-regulation of any one or more of the following genes: BCLAF1, BRCC3, GHR, IMMT, SENP7, SMC1A, PTPN11, SMARCE1, SRRT, SUMO1, and TNFSF10.

In accordance with a ninth aspect, the cutaneous defense is increasing a thickness of the skin, a relief of the epidermal rete ridges and/or a density of the collagen network in a papillary dermis.

Other objects, features and advantages of the described specific embodiments will become apparent to those skilled in the art from the following detailed description. It is to be understood, however, that the detailed description and specific examples, while indicating specific embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which.

DETAILED DESCRIPTION OF THE SPECIFIC EMBODIMENTS

Figure 1:
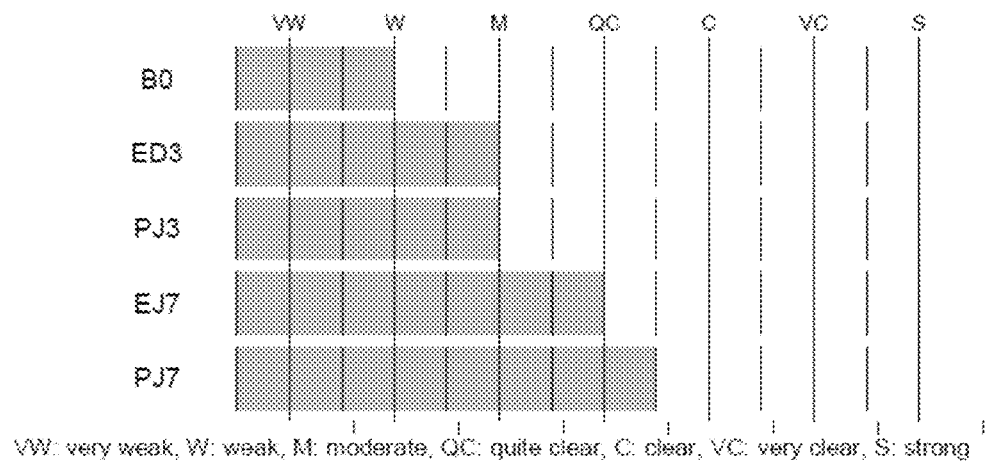
FIG. 1 represents the amount of catalase detected by immunostaining on skin explant specimens that had been treated for 7 days either with a Test Cream (P) or with a Base Cream (E). Immunostaining was performed at day 0 on control explant (B0; no treatment), and at day 3 and 7 on skin explant specimens treated with the Test Cream (PJ3, PJ7) or the Base Cream (ED3, EJ7).

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

*Brassica* Plant Extracts.

*Brassica* refers to a genus of plants in the mustard family, informally known as cruciferous vegetables, cabbages or mustard plants. In one specific embodiment, the compositions comprise one or a combination of *Brassica* plant extracts from *Brassica rapa, Brassica nigra, Brassica alba, Brassica carinata* and *Brassica oleracea*. In a specific embodiment, the compositions comprise one or a combination of the *Brassica* plant extracts from: *Brassica juncea, Brassica oleracea acephala* (kale and collard greens), *Brassica oleracea botrytis* (cauliflower, Romanesco broccoli and broccoflower), *Brassica oleracea capitata* (cabbage), *Brassica oleracea italica* (broccoli), *Brassica oleracea alboglabra* (Chinese broccoli), *Brassica oleracea gemmifera* (Brussel sprouts), and *Brassica oleracea Gongylodes* (kohlrabi). In a particularly specific embodiment, the compositions comprise all of the following *Brassica* plant extracts: *Brassica juncea, Brassica oleracea acephala, Brassica oleracea botrytis, Brassica oleracea capitata,* and *Brassica oleracea italica*.

The *Brassica* plant extracts contain isothiocyanates (ITCs) which are naturally occurring bioactive compounds:

$$R-N=C=S$$

Over 100 ITCs have been identified in plant extracts and many of the ITCs have demonstrated strong biological activities in cell culture, animal and human studies.

ITCs are believed to inhibit inflammation caused by UV light. ITCs are also believed to block the conversion of procarcinogens to carcinogens by down regulating the production of Phase I enzymes, such as cytochrome P450, which activate procarcinogens. ITCs are also believed to activate Phase II enzymes and antioxidant enzymes, such as glutathione 5-transferase, glutathione peroxidase, and glutathione reductase. When these Phase II enzymes are "switched on" by certain compounds, the body becomes more able to detoxify the carcinogens produced by Phase I enzymes. Phase II enzymes can attack the carcinogens directly or render them inert. Phase II enzymes are also believed to inactivate reactive oxygen species and reduce oxidative stress.

ITCs are believed to provide anti-inflammatory and antioxidant effect at very low levels. Significant anti-inflammatory activity has been observed with as little as 45 ppm ITCs. In a specific embodiment, the compositions described herein comprise at least 45 ppm ITCs, preferably 45 to 2,500 ppm, more preferably, 100 to 2,000 ppm and most preferably 500 to 1,500 ppm.

In a specific embodiment, the ITC comprises sulforaphane:

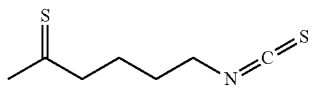

Sulforaphane (SFN), one of naturally occurring isothiocyanates (ITCs), has significant cancer chemopreventive potential. It modulates cell death, cell cycle, angiogenesis, susceptibility to carcinogens, invasion and metastasis and possesses antioxidant activities. It functions as an inhibitor of phase I enzymes and also as an inducer of phase II detoxification enzymes through different ways. Nrf2, as well as mitogen-activated protein kinase (MAPK), is regulated by SFN.

*Wasabia japonica* Extracts.

*Wasabia japonica* is a member of the Brassicaceae family which includes cabbages, horseradish and mustard. The chemical in *Wasabia japonica* that provides for its initial pungency is the volatile allyl isothiocyanate, which is produced by hydrolysis of natural rhizome thioglucosides (conjugates of the sugar glucose, and sulfur-containing organic compounds). The hydrolysis reaction is catalyzed by myrosinase and occurs when the enzyme is released on cell rupture caused by maceration—e.g., grating—of the plant's rhizome.

*Wasabia japonica* may be an additional source of ITCs as it comprises methylthioalkyl isothiocyanates, such as 6-methylthiohexyl isothiocyanate, 7-methylthioheptyl isothiocyanate, and 8-methylthiooctyl isothiocyanate. Research has shown that such isothiocyanates inhibit microbe growth, perhaps with implications for preserving food against spoilage and suppressing oral bacterial growth. Thus, *Wasabia japonica* root extract may be combined with the *Brassica* extracts to provide the desired level of ITCs as described above.

Turmeric (*Curcuma longa*) Extracts.

Turmeric is a rhizomatous herbaceous perennial plant of the ginger family, Zingiberaceae. The most important chemical components of turmeric are a group of compounds called curcuminoids, which include curcumin (diferuloylmethane), demethoxycurcumin, and bisdemethoxycurcumin. The best studied compound is curcumin, which constitutes 3.14% (on average) of powdered turmeric. In addition there are other important volatile oils such as turmerone, atlantone, and zingiberene. Some general constituents are sugars, proteins, and resins.

Curcuminoids are reported to be potent antioxidant and chemopreventive compounds due to their molecular structure. Certain metabolites and derivatives of curcuminoids have also demonstrated antioxidant activity, such as tetrahydrocurcuminoids (THC). THC is a hydrogenated product derived from curcuminoids and are believed to function as efficient antioxidant compounds. Derivatives of tetrahydrocurcuminoids include tetrahydrodiferuloylmethane, tetrahydrodemethoxydiferuloylmethane and tetrahydrobisdemethoxydiferuloylmethane

*Plantago lanceolata* Extract.

*Plantago lanceolata* is a species of the genus *Plantago* known by the common names ribwort plantain, English plantain, buckhorn plantain, narrowleaf plantain, ribleaf and lamb's tongue. *Plantago lanceolata* contains phenylethanoids, phenylpropanoids, acteoside, cistanoside F, lavanulifolioside, plantamajoside and isoacteoside. It also contains the iridoid glycosides aucubin and catapol.

The phenylpropanoids are a diverse family of organic compounds and are believed to provide protection from UV light. In a specific embodiment, the phenylproponaoid present in the composition is plantamajoside. In a specific embodiment, the compositions comprise *Plantago lanceolata* extract. In another specific embodiment, the compositions comprise one or more phenylpropanoids. In a further specific embodiment, the compositions comprise plantamajoside. The plantamajoside may be present in the composition in an amount of 100 to 2,500 ppm, preferably 250 to 2,000 ppm, and most preferably 500 to 1,500 ppm.

Black Paper (*Piper nigrum*) Extract.

*Piper nigrum* is a flowering vine in the family Piperaceae, cultivated for its peppercorn, which is usually dried and used as a spice and seasoning.

Tetrahydropiperine is a derivative of piperine, an alkaloid found in black pepper and long pepper. Derivatives of tetrahydropiperine, such as alkyltetrahydropiperines, dialkyltetrahydropiperines, alkoxylated tetrahydropiperine, hydroxylated tetrahydropiperine, halogenated tetrahydropiperine, alkyldihydropiperines, dialkyldihydropiperines, alkoxylated dihydropiperine, and halogenated dihydropiperine, may be used to formulate anti-inflammatory compounds, natural conditioning agents, anthelminthics, insecticides and drug actives. U.S. Pat. No. 6,849,645, entitled "Method of increased bioavailability of nutrients and pharmaceutical preparations with tetrahydropiperine and its analogues and derivatives" is incorporated by reference in its entirety as if fully set forth herein.

In a specific embodiment, the compositions comprise black pepper (*Piper nigrum*) extract. In another specific embodiment, the compositions comprise piperine, tetrahydropiperine, and/or derivatives and/or analogues of piperine and/or tetrahydropiperine.

*Bacopa* (Brahmi) *Monnieri* Extract.

*Bacopa monnieri* is a perennial, creeping herb native to the wetlands of southern India, Australia, Europe, Africa, Asia, and North and South America. *Bacopa monnieri* is believed to display antioxidant and cell-protective effects. It is also believed to inhibit acetylcholinesterase, activate choline acetyltransferase, and increase cerebral blood flow.

The best characterized compounds in *Bacopa monnieri* are dammarane types of triterpenoid saponins known as bacosides, with jujubogenin or pseudo jujubogenin moieties as aglycone units. Bacosides comprise a family of 12 known analogs. Novel saponins called bacopasides I-XII have been identified more recently. The alkaloids brahmine, nicotine, and herpestine have been catalogued, along with D-mannitol, apigenin, hersaponin, monnierasides I-III, cucurbitacins and plantainoside B.

*Bacopa monnieri* comprises bacoside A, which is believed to be a blend of bacoside A3, bacopacide II, bacopasaponin C, and a jujubogenin isomer of bacosaponin C. Bacoside A is believed to enhance antioxidation and to increase superoxide dismutase, catalase, and glutathione peroxidase activities.

In a specific embodiment, the compositions comprise *Bacopa monnieri* extract. In another specific embodiment, the compositions comprise one or more bacosides. In a further specific embodiment, the bacosides comprise bacoside A.

Milk Thistle (*Silybum marianum*) Extract.

Milk thistle is an annual or biennial plant of the Asteraceae family. This fairly typical thistle has red to purple flowers and shiny pale green leaves with white veins. Originally a native of Southern Europe to Asia, it is now found throughout the world.

Silymarin, a flavonoid complex that can be extracted from the seeds of milk thistle, is composed of three isomers. A standard milk thistle extract contains a mixture of flavonolignans, such as silymarin, silibinin, silychristin, silydianin, dehydrosilyin, deoxysilycistin, deoxysilydianin, siladrin, silybinome, silyhermin, and neosilyhermin. Other constituents include dehydrosilybin, desoxy-silydianin, and silybinomer.

Milk thistle extracts have been demonstrated to have antibacterial activity and anticancer effects. It is believed that topically applied silymarin reduces UVB and chemically induced carcinogenesis.

In a specific embodiment, the compositions comprise milk thistle (*Silybum marianum*) extract. In another specific embodiment, the compositions comprise one or more flavinolignans. In a further specific embodiment, the compositions comprise one or more flavinolignans selected from the group consisting of silymarin, silibinin, silychristin, silydianin, dehydrosilyin, deoxysilycistin, deoxysilydianin, siladrin, silybinome, silyhermin, and neosilyhermin.

Tea Extracts.

A variety of tea leaf extracts may be incorporated in the compositions. Preferably, the tea extract is derived from one or a combination of *Camellia oleifera* extract, *Camellia sinensis* extract, green tea extract and white tea extract. The tea extract is believed to contain many useful anti-oxidant compounds.

The cardinal antioxidative ingredient in the green tea extract is green tea catechins (GTC), which comprise four major epicatechin derivatives; namely, epicatechin (EC), epigallocatechin (EGC), epicatechin gallate (ECG), and epigallocatechin gallate (EGCG).

Other components include three kinds of flavonoids, known as kaempferol, quercetin, and myricetin. A remarkably higher content of myricetin is detected in tea and its extracts than in many other plants, and this high concentration of myricetin may have some implications with the bioactivity of tea and its extracts.

Additional Agents.

Specific embodiments of the compositions described herein may include any one or a combination of additional ingredients. Non-limiting examples of additional ingredients include cosmetic, sunscreen, moisturizing, antioxidant, structuring, emulsifying, silicone-containing, thickening, and/or pharmaceutical agents and also plant oils.

Cosmetic Agents.

The compositions described herein may additionally include any one or a combination of cosmetic agents. The CTFA International Cosmetic Ingredient Dictionary and Handbook (2008), 12th Edition, describes a wide variety of non-limiting cosmetic ingredients that may be used in compositions described herein. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents (including, e.g., isopentyldiol), moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), plant oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, *ginkgo biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and mannitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, palmitoyl peptides, protein hydrolysates and dipotassium glycyrrhizate), thickening agents (e.g., substances which that may increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes).

Sunscreen Agents.

The compositions described herein may additionally include any one or a combination of sunscreen agents, including chemical and physical sunblocks. Non-limiting examples of chemical sunblocks that may be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). The compositions described herein may have UV-A and UV-B absorption properties. The compositions may have a sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

Moisturizing Agents.

The compositions described herein may additionally include any one or a combination of moisturizing agents. Non-limiting examples of moisturizing agents that may be used with the compositions described herein include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, *aloe barbadensis, aloe barbadensis* extract, *aloe barbadensis* gel, *althea officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *eucalyptus globulus* oil, evening primrose (*oenothera biennis*) oil, fatty acids, tructose, gelatin, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, *matricaria* (*chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

Antioxidant Agents.

The compositions described herein may additionally include any one or a combination of antioxidant agents, such as acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Structuring Agents.

The compositions described herein may additionally include any one or a combination of structuring agents. Structuring agents, in certain aspects, assist in providing rheological characteristics to the composition to contribute to the composition's stability. In other aspects, structuring agents may also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof Emulsifying Agents.

The compositions described herein may additionally include any one or a combination of emulsifying agents. Emulsifiers may reduce the interfacial tension between phases and improve the formulation and stability of an emulsion. The emulsifiers may be nonionic, cationic, anionic, and zwitterionic emulsifiers. Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

Silicone Containing Agents.

The compositions described herein may additionally include any one or a combination of silicone containing agents. In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones may be synthesized into a wide variety of materials. They may vary in consistency from liquid to gel to solids.

The silicone containing compounds that may be used in the compositions described herein include those described in this specification or those known to a person of ordinary skill in the art. Non-limiting examples include silicone oils (e.g., volatile and non-volatile oils), gels, and solids. In specific aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that may be used in the compositions described herein include those available from General Electric Co., Silicone Products Div., Waterford, N.Y. and SWS Silicones Div. of Stauffer Chemical Co., Adrian, Mich.

Plant Oils.

The compositions described herein may additionally include any one or a combination of plant oils. Plant oils include oils derived from herbs, flowers, trees, and other plants. Such oils are typically present as tiny droplets between the plant's cells, and may be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many plant oils are colorless, but with age they may oxidize and become darker. Plant oils are insoluble in water and are soluble in alcohol, ether, fixed oils (vegetal), and other organic solvents. Typical physical characteristics found in plant oils include boiling points that vary from about 160° to 240° C. and densities ranging from about 0.759 to about 1.096.

Plant oils typically are named by the plant from which the oil is found. For example, rose oil or peppermint oil are derived from rose or peppermint plants, respectively. Non-limiting examples of plant oils that may be used in the compositions described herein include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other plant oils known to those of skill in the art are also contemplated as being useful when formulated in the compositions described herein.

Thickening Agents.

The compositions described herein may additionally include any one or a combination of thickening agents. Thickening agents, including thickener or gelling agents, include substances that may increase the viscosity of a composition. Thickeners include those that may increase the viscosity of a composition without substantially modifying the efficacy of the active ingredient within the composition. Thickeners may also increase the stability of the compositions described herein.

Non-limiting examples of additional thickening agents that may be used in the compositions described herein include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; and 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that may be used with the compositions described herein include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof Pharmaceutical Agents.

The compositions described herein may additionally include any one or a combination of pharmaceutical agents. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

EXAMPLE 1

Composition Sets

The compositions may be formulated as a cleanser, skin lotion, eye serum, and cream, which may be provided separately or together as a set.

Cleanser.

In an exemplary embodiment, the cleanser comprises *Bacopa monnieri* (*Brahmi*) extract, *Silybum marianum* (milk thistle) extract, *Piper nigrum* (pepper) seed extract, *Camellia oleifera* leaf extract, and *Curcuma longa* (turmeric) root extract. The amount ratio of these ingredients is preferably at least 5:5:5:1:1 of *Bacopa monnieri* extract, *Silybum marianum* extract, *Camellia oleifera* leaf extract, *Curcuma longa* root extract, and *Piper nigrum* seed extract, respectively.

The cleanser may further comprise one or a combination of additional ingredients, including water, acrylates copolymer, sodium cocoyl isethionate, sodium methyl cocoyl taurate, aminomethyl propanol, hydroxyl guar hydroxypropyltrimonium chloride, tetrasodium glutamate diacetate, panthenol, cetearyl alcohol, ceteareth-20, phentyl trimethicone, cyclomethicone, hydrogenated lecithin, phenoxyethanol, caprylyl glycol, ethylhexylglycerin, hexylene glycol, alpha glucan oligosaccharide, xylitylglucoside, anhydroxylitol, *Aloe barbardensis* leaf juice, algae extract, and phenoxyethanol.

Skin Lotion.

In an exemplary embodiment, the skin lotion comprises *Brassica Juncea* extract, *Brassica oleracea italica* sprout extract, *Brassica oleracea capitata* leaf extract, *Brassica oleracea botrytis* extract, *Brassica oleracea acephala* leaf extract, *Wasabia japonica* root extract, *Bacopa monnieri* (Bramhi) extract, *Silybum marianum* (Milk Thistle) hydroalcoholic extract (seeds), *Piper Nigrum* (Pepper) Seed Extract, *Camellia Oleifera* (Green Tea) hydroalcoholic extract (leaf), and *Curcuma longa* (Turmeric) hydroalcoholic extract (root).

The skin lotion may further comprise one or a combination of additional ingredients, including water, glycerin, *Astragalus membranaceus* root extract, *Atractyloides macrocephaly* root extract, *Bupleurum Falcatum* root extract, phenoxyethanol, xylitylglucoside, anhydroxylitol, xylitol, isoceteth-20, tetrasodium glutamate diacetate, sodium hydroxide, phenoxyethanol, ethylhexylglycerin, xanthan gum, and malachite.

Eye Serum.

In an exemplary embodiment, the eye serum comprises *Brassica Juncea* extract, *Brassica oleracea italica* sprout, *Brassica oleracea capitata* leaf extract, *Brassica oleracea botrytis* extract, *Brassica oleracea acephala* leaf extract, *Wasabia japonica* root extract, *Plantago lanceolata* leaf extract, *Bacopa monnieri* (Bramhi) extract, *Silybum marianum* (Milk Thistle) hydroalcoholic extract (seeds), *Piper Nigrum* (Pepper) seed extract, *Camellia oleifera* (Green Tea) hydroalcoholic extract (leaf), and *Curcuma longa* (Turmeric) hydroalcoholic extract (root).

The eye serum may further comprise one or a combination of additional ingredients, including water, glycerin, phenoxyethanol, caprylyl glycol, carbomer, acrylates/C10-30 alkyl acrylate crosspolymer, *Albizia julibrissin* bark extract, darutoside, *Aloe barbardensis* leaf juice, algae extract, allantoin, panthenol, ethylhexyl palmitate, polysorbate 20, tocopheryl acetate, alpha glucan oligosaccharide, xanthan gum, citric acid, sodium hydroxide, ethylhexylglycerin, hexylene glycol, and tetrasodium glutamate diacetate.

Anti-Aging Cream.

In an exemplary embodiment, the cream comprises *Brassica juncea* extract, *Brassica oleracea italica* (broccoli) sprout extract, *Brassica oleracea capitata* (cabbage) leaf extract, *Brassica oleracea botrytis* (cauliflower) extract, *Brassica oleracea acephala* leaf (collard greens) extract, *Wasabia japonica* root extract, *Bacopa monnieri* (*Brahmi*) extract, *Silybum marianum* (Milk Thistle) extract, Black pepper extract (Tetrahydropiperine), Turmeric extract (Tetrahydrocurcuminoids), *Plantago lanceolata* leaf extract, and *Camellia oleifera* or *sinensis* extract.

The anti-aging cream may further comprise one or a combination of additional ingredients, including glycerin, water, butylene glycol, carbomer, polysorbate 20, palmitoyl oligopeptide, palmitoyl tetrapeptide-7, phenoxyethanol, glyceryl stearate, cetearyl alcohol, sodium stearoyl lactylate, pentylene glycol, calcium hydroxymethionine, 3-aminopropane sulfonic acid, polysorbate 20, hydroxyethylcellulose, isopentyldiol, dimethicone, betaine, SD Alcohol 40-B, xanthan gum, citric acid, glycolipids, soybean phytosterols, sodium hyaluronate, sea salt, carrageenan, *Santalum album* (Sandalwood) extract, *Phellodendron amurense* bark extract, *Hordeum distichon* (Barley) extract, *Olea europaea* (Olive) fruit unsaponifiables, caprylyl glycol, ethylhexylglycerin, eexylene glycol, MPC-Milk Peptide Complex/Whey Protein, tetrahexyldecyl ascorbate, tetrasodium EDTA, tocopheryl acetate, tocopherol, *Aloe barbadensis* leaf juice, and panthenyl triacetate.

EXAMPLE 2

Anti-Oxidant Capacity of Topical Compositions

The topical application of a test antioxidant cream comprising twelve (12) of oxidative stress reducing agents ("Test Cream") was applied to human skin explants of a middle-aged female donor twice a day for 7 days. The twelve (12) oxidative stress reducing agents contained in the Test Cream included the five (5) *Brassica* plant extracts, *Brassica juncea*, *Brassica oleracea acephala*, *Brassica oleracea botrytis*, *Brassica oleracea capitata*, and *Brassica oleracea italica*; *Wasabia japonica*; tetrahydrocurcuminoids; black tetrahydropiperine; *Camellia oleifera* leaf extract; *Plantago lanceolata* leaf extract; *Bacopa monnieri* extract; and *Silybum marianum* extract. Similarly a Base Cream excluding these (12) oxidative stress reducing agents, but otherwise having the same base ingredients as the Test Cream, was applied to skin explants of same donor under the same conditions. Control explants, which were not treated by the Test or the Base Creams, were also prepared.

Gene Expression Results.

A gene expression profile study was performed using Agilent technology microarrays, which targets more than 62,976 probes without controls derived from the National Center for Biotechnology Information Reference Sequence (NCBI) RefSeq. These microarrays were hybridized to Cy3-cRNAs synthesized using total RNAs extracted from human skin explants treated for one day with the Test Cream, Base Cream or left untreated for different incubation times (3, 9, and 24 hours). The goal was to identify the genes which were up- or down-regulated by the topical application of the 12 oxidative stress reducing and DNA repair agents in the Test Cream. The genes were selected according to the fold change method. The modulated genes had to be at least 1.5 fold greater between the base-treated and the test-treated samples to be positively activated or less than 0.55 fold change between control and treated samples to be negatively activated.

Among the Nrf2 target genes, a significant overexpression of catalase (CAT) was seen at all 3 time points (3, 9 and 24 hours), whereas a slight up-regulation of Activating Transcription Factor 3 (ATF3) and peroxiredoxin 3 (PRDX3) was observed at 9 hours.

Catalase (CAT) is a key antioxidant enzyme in the body defense against oxidative stress. CAT is a heme enzyme that is present in the peroxisome of nearly all aerobic cells. Catalase converts the reactive oxygen species hydrogen peroxide to water and oxygen and thereby mitigates the toxic effects of hydrogen peroxide. In a wide range of cell types and particularly in the skin, CAT contributes to the maintenance of genomic integrity and preservation of ROS (reactive oxygen species) homeostasis by scavenging and detoxifying hydrogen peroxide.

Next, a selection of genes whose expression was significantly expressed in response to the test cream was undertaken according to the following criteria:

Intensity values below the background (according to Agilent criteria) were removed in all conditions treated with the test cream Ratios were deduced from the intensity value of a condition treated with the test cream versus intensity value of a condition treated with the base cream These ratios were calculated for all combinations (triplicated test and control conditions for each time point), leading to 9 ratios for each time point.

Among genes presenting a fold change ≥1.25, those presenting a fold change ≥1.45 in at least 7 ratios out of 9 in at least one time point (3, 9 or 24 h) were considered for submission to PredictSearch analysis. Such criteria lead to select 282 annotated genes.

Within this set of genes, among the top ten up-regulated genes, those, which were co-cited with CAT using PredictSearch were analyzed. Five genes were found highly induced in response to the product and encodes, according to the alphabetic order: ABL2/ARG (c-abl oncogene 2, non-receptor tyrosine kinase), GHR (growth hormone receptor), IMMT (inner membrane protein, mitochondrial), PIK3CA (phosphatidylinositol-4,5-bisphosphate 3-kinase, catalytic subunit alpha), and RALBP1 (ralA binding protein 1). ABL2/ARG is believed to present a direct functional link with CAT.

Selected genes were submitted to PredictSearch analysis to determine whether they could be integrated within relevant functional networks. PredictSearch is a powerful data and text mining software that searches and retrieves through millions of scientific publications correlations between genes and biological processes or diseases. The functional correlation based on the Fisher test, allows statistical co-citation analysis of annotated key words in order to define relationships between genes, biological processes and concepts, metabolites, diseases, and tissues/cells/organs.

Indeed, recent studies have shown that CAT activity is stimulated by ABL2/ARG, a member of the Abelson family of nonreceptor tyrosine protein kinases, highly similar to c-Abl (c-abl oncogene 1 protein). It has been demonstrated that, in addition to stimulating CAT activity, c-Abl and ABL2/ARG promote CAT degradation in the oxidative stress response. Moreover, $H_2O_2$ interacts and induces binding of c-Abl and ABL2/ARG to CAT. The functional significance of the interaction was supported by the demonstration that cells deficient in both c-Abl and ABL2/ARG exhibit substantial increases in $H_2O_2$ levels. In addition, c-abl–/– ABL2/ARG –/– cells exhibited a marked increase in $H_2O_2$-induced apoptosis compared with that found in the absence of either kinase. These findings indicate that c-Abl and ABL2/ARG regulate catalase and that this signaling pathway is of importance to apoptosis in the oxidative stress response.

ABL2/ARG plays a role in cytoskeletal rearrangements through its C-terminal F-actin- and microtubule-binding sequences. Investigating the expression profile of protein tyrosine kinases (PTKs) in normal human epidermal keratinocytes (NHEK) in response to UV-A and UV-B, it has been found that ABL2/ARG was the PTK with the highest prevalence (30% of all PTKs). UV-A led to a further induction of ABL2/ARG expression reaching nine-fold mRNA baseline expression at 17 h after irradiation. UV-B was followed by an initial down-regulation and a subsequent increase in ABL2/ARG mRNA reaching five-fold baseline levels after 24 h. According to these observations, ABL2/ARG appears to have a major role in the response of keratinocytes to UV.

On the other hand, ABL2/ARG is believed to associate with the proapoptotic Siva-1 protein. The functional significance of the ABL2/ARG-Siva-1 interaction is supported by the finding that ABL2/ARG is activated also by oxidative stress and that this response involves ABL2/ARG-mediated phosphorylation of Siva-1 on Tyr(48). The proapoptotic effects of Siva-1 are accentuated in cells stably expressing ABL2/ARG and are inhibited in ABL2/ARG-deficient cells. These proapoptotic effects of Siva-1 are abrogated by mutation of the Tyr(48) site and the apoptotic response to oxidative stress is attenuated in ABL2/ARG-deficient cells, a defect corrected by reconstituting ABL2/ARG expression. These findings support a model in which the activation of ABL2/ARG by oxidative stress induces apoptosis by a Siva-1-dependent mechanism.

Another factor, which is believed to interact with ABL2/ARG, is RAD51. RAD51 plays important roles in repair of DNA double strand breaks (DSBs). It has been reported that ionizing radiation (IR)-induced RAD51 focus formation is reduced in ABL2/ARG-deficient cells generated from a chicken B cell line by targeted disruption. This is consistent with the findings that ABL2/ARG-deficient cells display hypersensitivity to IR, elevated frequencies of IR-induced chromosomal aberrations, and reduced targeted integration frequencies. All of these abnormalities in DNA damage repair are also observed in cells deficient in ATM (ataxia telangiectasia mutated). ATM is a protein involved in DNA DSB repair and is known to interact with and phosphorylate RAD51, In response to DNA damages, ABL2/ARG stimulates homologous recombinational (HR) DNA repair by phosphorylating RAD51.

Altogether, these observations suggest that the product mimics the effects of UV or oxidative stress, and consequently leads to stimulate the cutaneous intrinsic defense (i.e. keratinocytes, fibroblasts etc.) against these stresses. The protective effect may rely on ABL2/ARG, which interacts with either CAT to reduce the oxidative defects or with RAD51 to stimulate DNA repair processes.

Such an activity triggered by the product is supported by the role played in DNA DSB repair/genome stability of several proteins coded by up-regulated genes such as BCLAF1, BRCC3, GHR, IMMT, SENP7, and SMC1A.

BCLAF1, BCL2-associated transcription factor 1, encodes a transcriptional repressor that interacts with several members of the BCL2 family of proteins. Overexpression of this protein induces apoptosis, which can be suppressed by co-expression of BCL2 proteins. BCLAF1 shows, only under high-dose radiation, enhanced association with γH2AX, a phosphorylated form of the histone H2A variant, H2AX, which has a key role in the cellular response to DNA double-strand breaks. In acutely irradiated cells, BCLAF1 promotes apoptosis of irreparable cells through disturbing p21-mediated inhibition of Caspase/cyclin E-dependent, mitochondrial-mediated pathways. Meanwhile, BCLAF1 facilitates non-homologous end joining (NHEJ)-based DNA DSB repair in surviving cells.

SENP7, Sumo1/sentrin specific peptidase 7, is believed to be required for chromatin relaxation in response to DNA damage, for homologous recombination repair and for cellular resistance to DNA-damaging agents. SENP7 processes SUMO precursors, as SUMO1, involved in sumoylation, a reversible posttranslational modification of proteins. The sumoylation, which results from the addition of small ubiquitin-like SUMO proteins, is required for many cellular processes and SUMO conjugation is known to occur in response to double-stranded DNA breaks in mammalian cells.

SMC1A, structural maintenance of chromosome 1A, is part of the cohesin multiprotein complex required for sister chromatid cohesion. Proper cohesion of sister chromatids is a prerequisite for the correct segregation of chromosomes during cell division. This complex is composed partly of two structural maintenance of chromosomes (SMC) proteins, SMC3 and either SMC1B or SMC1A. Following DNA damage, cohesin accumulates at and promotes the repair of DNA DSBs.

Recent work in yeast has shown that DNA DSBs induce the recruitment of cohesin to the damage site and lead to the de novo formation of cohesion at this site. In mammalian cells phosphorylation of the cohesin subunit SMC1A by the protein kinase ATM has been shown to be important for DNA repair. The SMC1A protein appears to be a particularly important target of the ATM kinase, playing critical roles in controlling DNA replication forks and DNA repair after the damage.

Moreover, SMC1A, thought to be an important part of functional kinetochores, interacts with BRCA1, which can associate with BRCC3. The later allows the accumulation of BRCA1 at the DNA DBS sites.

A major role for the NBS1 and BRCA1 proteins appears to be in the recruitment of an activated ATM kinase molecule to the sites of DNA breaks so that ATM can phosphorylate SMC1A. The phosphorylation of NBS1 by ATM is required for the phosphorylation of SMC1A, establishing the role of NBS1 as an adaptor in the ATM/NBS1/SMC1A pathway. Indeed, NBS1 is part of the Mre11/RAD503/NBS1 complex, which plays a central role in coordinating the cellular response to DSBs. Within this complex, it has been shown that RAD503, phosphorylated by ATM, plays a key regulatory role as an adaptor for specific ATM-dependent downstream signaling.

In addition, phosphorylation of the SMC1A subunits contributes to DNA damage-induced cell cycle checkpoint regulation. The ATM-dependent phosphorylation of SMC1A and SMC3 is mediated by H2AX, 53BP1 and MDC1 and phosphorylation of SMC1A is required for an increased mobility after DNA damage in G2-phase cells, suggesting that ATM-dependent phosphorylation facilitates mobilization of the cohesin complex after DNA damage.

BRCC3/BRCC36, BRCA1/BRCA2-containing complex, subunit 3, encodes a subunit of the BRCA1-BRCA2-containing complex (BRCC), which is an E3 ubiquitin ligase. This complex plays a role in the DNA damage response, where it is responsible for the stable accumulation of BRCA1 at DNA break sites. The component encoded by this gene can specifically cleave Lys 63-linked polyubiquitin chains, and it regulates the abundance of these polyubiquitin chains in chromatin. A pathway, involving RAP80-BRCC3/BRCC36 as a de-ubiquitinating enzyme complex, required to reverse RNF8-Ubc13 dependent ubiquitination events on chromatin flanking DNA DSBs has been identified.

GHR, growth hormone receptor, encodes a member of the type I cytokine receptor family, which is a transmembrane receptor for growth hormone. Binding of growth hormone to the receptor leads to receptor dimerization and the activation of an intra- and intercellular signal transduction pathway leading to growth. It has been described that the increased survival in response to radiation and bleomycin treatment induced by growth hormone correlates with an enhanced ability of the cells to repair damaged DNA. As in aging animals, the expression of IGF-1 receptor and GHR is attenuated, resulting in cellular resistance to IGF-1.

The accumulation of stochastic DNA damage throughout an organism's lifespan is thought to contribute to aging. Conversely, aging seems to be phenotypically reproducible and regulated through genetic pathways such as the insulin-like growth factor-1 (IGF-1) and growth hormone (GH) receptors, which are central mediators of the somatic growth axis. It has been reported that persistent DNA damage in primary cells from mice elicits changes in global gene expression similar to those occurring in various organs of naturally aged animals.

It has been shown that IMMT, inner membrane protein, mitochondrial/mitofilin, interacts with poly(ADP-ribose) polymerase-1 (PARP-1), which is a predominantly nuclear enzyme that exerts numerous functions in cellular physiology and pathology, from maintenance of DNA stability to transcriptional regulation. IMMT promotes and is required for PARP-1 mitochondrial localization. Depletion of either PARP-1 or Mitofilin, which abrogates the mitochondrial localization of the enzyme, leads to the accumulation of mtDNA damage (19762472).

At this point, the results confirm that the Test Cream mimics effects similar to those triggered by a stress such as UV or oxidative stress. However, based on the top ten regulated genes, the main effects seem to be related to the intrinsic protective response of the cell against DNA damage and in particular DNA double strand breaks as illustrated by SENP7 and SUMO1. The upstream signaling is likely depending on ATM or ATM-like activities, which involved ABL2/ARG and RAD503. Interestingly, c-ABL, highly similar to ABL2/ARG, and ATM are implicated differently in cell responses to DNA damage and oxidative stress, although both required PKC to trigger these effects. These pathways lead to the activation of a strong DNA repair response targeting SMC1A, which is a component of the DNA damage response network that functions as an effector in the ATM/NBS1-dependent S-phase checkpoint pathway. For instance, deficiency of c-ABL and deficiency of ATM differentially altered cell responses to oxidative stress via cell death and distinct effects on NRF2.

Among the second rank of highly up-regulated genes, only WDR3, WD repeat domain 3, is believed to be related to DNA repair.

DNA damage response is crucial for maintaining genomic integrity and preventing cancer by coordinating the activation of checkpoints and the repair of damaged DNA. Central to DNA damage response are the two checkpoint kinases ATM, as already mentioned, and ATR that phosphorylate a wide range of substrates. RING finger and WD repeat domain 3 (RFWD3) was initially identified as a substrate of ATM/ATR from a proteomic screen. Subsequent studies showed that RFWD3 is an E3 ubiquitin ligase that ubiquitinates p53 in vitro and positively regulates p53 levels in response to DNA damage. RFWD3 associates with replication protein A (RPA), a single-stranded DNA-binding protein that plays essential roles in DNA replication, recombination, and repair. Binding of RPA to single-stranded DNA (ssDNA), which is generated by DNA damage and repair, is essential for the recruitment of DNA repair factors to damaged sites and the activation of checkpoint signaling. RFWD3 is physically associated with RPA and rapidly localizes to sites of DNA damage in a RPA-dependent manner. Furthermore, DNA damage-induced phosphorylation of RPA and RFWD3 is dependent upon each other. Consequently, loss of RFWD3 results in the persistent foci of DNA damage marker γH2AX and the repair protein Rad51 in damaged cells. These findings suggest that RFWD3 is recruited to sites of DNA damage and facilitates RPA-mediated DNA damage signaling and repair.

Although a modulation of RFWD3 was not observed in our study, the up-regulation of a related member, WDR3, WD repeat domain 3, was detected. WDR3 encodes a nuclear protein containing 10 WD repeats. WD repeats are approximately 30- to 40-amino acid domains containing several conserved residues, which usually include a trp-asp at the C-terminal end. Proteins belonging to the WD repeat family are involved in a variety of cellular processes, including cell cycle progression, signal transduction, apoptosis, and gene regulation.

Insulin-like growth factor-I (IGF-I) signaling is strongly associated with cell growth and regulates the rate of synthesis of the rRNA precursor, the first and the key stage of ribosome biogenesis. IGF-I induces expression of WDR3 in transformed cells. WDR3 has an essential function in 40 S ribosomal subunit synthesis and in ribosomal stress signaling to p53-mediated regulation of cell cycle progression in cancer cells.

Two other genes present in the top ten up-regulated genes are related to oxidative stress. PIK3CA, phosphatidylinositol 3-kinase is known to be involved in the response to oxidative stress and to act upstream of the NRF2 cascade. PIK3CA is composed of an 85 kDa regulatory subunit and a 110 kDa catalytic subunit. The protein encoded by PIK3CA represents the catalytic subunit, which uses ATP to phosphorylate PtdIns, PtdIns4P and PtdIns(4,5)P2. PIK3CA has been found to be oncogenic and has been implicated in cervical cancers.

Nuclear factor erythroid 2-related factor 2 (Nrf2) is a redox-sensitive transcription factor regulating expression of a number of cytoprotective genes. Apigenin (APG) an anticancer drug, dramatically reduced Nrf2 expression at both the messenger RNA and protein levels through down-regulation of PIK3CA/Akt pathway, leading to a reduction of Nrf2-downstream genes.

To counteract ROS- and electrophile-mediated injury, cells can induce a number of genes encoding phase II detoxifying enzymes and antioxidant proteins. A cis-acting transcriptional regulatory element, designated as antioxidant response element (ARE) or electrophile response element (EpRE), mediates the transcriptional activation of genes such as heme oxygenase-1, gamma-glutamylcysteine synthethase, thioredoxin reductase, glutathione-S-transferase and NAD(P)H: quinone oxidoreductase. Other antioxidant enzymes such as superoxide dismutase and catalase and non-enzymatic scavengers such as glutathione are also involved in scavenging ROS. Nrf2 plays an important role in ARE-mediated antioxidant gene expression. Kelch-like ECH-associated protein-1 (Keap1) normally sequesters Nrf2 in the cytoplasm in association with the actin cytoskeleton, but upon oxidation of cysteine residues Nrf2 dissociates from Keap1, translocates to the nucleus and binds to ARE sequences leading to transcriptional activation of antioxidant and phase II detoxifying genes. Protein kinase C (PKC), mitogen-activated protein kinases (MAPKs) and PIK3CA have been implicated in the regulation of Nrf2/ARE signaling and its protective activity against sustained oxidative stress.

RALBP1/RLIP76, ralA1 binding protein 1, plays a role in receptor-mediated endocytosis and is a downstream effector of the small GTP-binding protein RAL. Small G proteins, such as RAL, have GDP-bound inactive and GTP-bound active forms, which shift from the inactive to the active state through the action of RALGDS, which in turn is activated by RAS. RALBP1 is a cell surface protein that catalyzes the extrusion from the cell of reduced glutathione (GSH) conjugates, a process, which is part of an important detoxification mechanism. In addition, RALBP1 has been found to be involved in mitochondrial fission (ensuring the appropriate distribution of mitochondria to daughter cells) whose loss is associated with mitochondrial dysfunction, including impaired energy production.

Among the 61 remaining genes out of 82 induced upon treatment at all time points according to the selected criteria, genes co-cited with "DNA repair" and/or "oxidative stress" were analyzed.

CCNG2, cyclin G2, encodes an unconventional cyclin homolog, cyclin G2 (CycG2), linked to growth inhibition. Its expression is repressed by mitogens but up-regulated during cell cycle arrest responses to anti-proliferative signals. CCNG2 overexpression induces a p53-dependent G(1)/S phase cell cycle arrest in HCT116 cells, and this arrest response also requires the DDR checkpoint protein kinase Chk2 In accord with this finding, CCNG2 expression increases phosphorylation of Chk2 on threonine 68. Moreover, DNA double strand break-inducing chemotherapeutics stimulate CCNG2 expression and correlate its up-regulation with checkpoint-induced cell cycle arrest and phospho-modification of proteins in the ataxia telangiectasia mutated (ATM) and Rad3-related (ATR) signaling pathways.

CENPC1, centromere protein C 1 is a centromere autoantigen and a component of the inner kinetochore plate. The protein is required for maintaining proper kinetochore size and a timely transition to anaphase.

A broad spectrum of mutations in PTEN, encoding a lipid phosphatase that inactivates the PIK3CA/AKT pathway, is found associated with primary tumors. A nuclear function for PTEN in controlling chromosomal integrity has been reported. Disruption of PTEN leads to extensive centromere breakage and chromosomal translocations. PTEN was found localized at centromeres and physically associated with CENPC1. PTEN acts on chromatin and regulates expression of RAD51, which reduces the incidence of spontaneous DSBs. These results demonstrate that PTEN plays a fundamental role in the maintenance of chromosomal stability through the physical interaction with centromeres and control of DNA repair. It has been proposed that PTEN acts as a guardian of genome integrity.

DHX40/PAD/DDX40 encodes a member of the DExH/D box family of ATP-dependent RNA helicases that have an essential role in RNA metabolism, such as pre-mRNA splicing, ribosome biogenesis, and others. It contained a DEAH (Asp-Glu-Ala-His) sequence motif and other conserved motifs. A close member of this family, DEAH box polypeptide 30 isoform 1, together with PARP, poly(ADP-ribose) polymerase-1, both involved in DNA repair, was found to interact transiently with H2AX after ionizing radiation.

NAMPT, nicotinamide phosphoribosyltransferase, encodes a protein that catalyzes the condensation of nicotinamide with 5-phosphoribosyl-1-pyrophosphate to yield nicotinamide mononucleotide, one step in the biosynthesis of nicotinamide adenine dinucleotide. The protein belongs to the nicotinic acid phosphoribosyltransferase (NAPRTase) family and is thought to be involved in many important biological processes, including metabolism, stress response and aging.

DNA DSB is the most severe form of DNA damage, which is repaired mainly through high-fidelity homologous recombination (HR) or error-prone non-homologous end joining (NHEJ). Defects in the DNA damage response lead to genomic instability and ultimately predispose organs to cancer. NAMPT physically associates with CtIP and DNA-PKcs/Ku80, which are key factors in HR and NHEJ, respectively. Depletion of NAMPT by small interfering RNA (siRNA) leads to defective NHEJ-mediated DSB repair and enhances HR-mediated repair. Thus, it has been suggested that NAMPT is a suppressor of HR-mediated DSB repair and an enhancer of NHEJ-mediated DSB repair, contributing to the acceleration of cellular senescence.

NCOR1, nuclear receptor corepressor 1, encodes a protein that mediates ligand-independent transcription repression of thyroid-hormone and retinoic-acid receptors by promoting chromatin condensation and preventing access of the transcription machinery. It is part of a complex, which also includes histone deacetylases such as Hdac3, and transcriptional regulators similar to the yeast protein Sin3p.

Hdac3 is essential for efficient DNA replication and DNA damage control. Deletion of Hdac3 impaired DNA repair and greatly reduced chromatin compaction and heterochromatin content. These defects corresponded to increases in histone H3K9, K14ac; H4K5ac; and H4K12ac in late S phase of the cell cycle. Whereas HDAC3 expression was downregulated in only a small number of human liver cancers, the mRNA levels of the HDAC3 cofactor NCOR1 were reduced in one-third of these cases. siRNA targeting of NCOR1 and SMRT (NCOR2) increased H4K5ac and caused DNA damage, indicating that the HDAC3/NCOR/SMRT axis is critical for maintaining chromatin structure and genomic stability.

Cellular senescence is one of the key strategies to suppress expansion of cells with mutations. Senescence is induced in response to genotoxic and oxidative stress. It has been shown that the transcription factor Bach1 (BTB and CNC homology 1, basic leucine zipper transcription factor 1), which inhibits oxidative stress-inducible genes, is a crucial negative regulator of oxidative stress-induced cellular senescence. Bach1-deficient murine embryonic fibroblasts showed a propensity to undergo more rapid and profound p53-dependent premature senescence than control wild-type cells in response to oxidative stress. Bach1 formed a complex that contained p53, histone deacetylase 1 and NCOR1. Bach1 was recruited to a subset of p53 target genes and contributed to impeding p53 action by promoting histone deacetylation. Because Bach1 is regulated by oxidative stress and heme, it is likely that Bach1 connects oxygen metabolism and cellular senescence as a negative regulator of p53.

Of note, in contrast to all the genes described above, HNRNPA2B1 encodes a protein whose functions act to block DNA repair.

HNRNPA2B1 belongs to the A/B subfamily of ubiquitously expressed heterogeneous nuclear ribonucleoproteins (hnRNPs). The hnRNPs are RNA binding proteins and they complex with heterogeneous nuclear RNA (hnRNA). These proteins are associated with pre-mRNAs in the nucleus and appear to influence pre-mRNA processing and other aspects of mRNA metabolism and transport. While all of the hnRNPs are present in the nucleus, some seem to shuttle between the nucleus and the cytoplasm.

Genome-wide mapping of DNA DSBs revealed that DSB hot spots are scattered along chromosomes and delimit protected 50-250 kb DNA domains. It has be determined that about 30% of the domains (denoted forum domains) possess coordinately expressed genes and that PARP1 and HNRNPA2B1 specifically bind DNA sequences at the forum domain termini.

Inactivation of the breast cancer susceptibility gene 1 (BRCA1) plays a significant role in the development of a subset of familial breast and ovarian cancers, but increasing evidence points to a role also in sporadic tumors. BRCA1 is a multifunctional nuclear protein involved in the regulation of many nuclear cellular processes, including DNA repair, cell cycle, transcription and chromatin remodeling. Identification of proteins participating in the BRCA1 network leads to find HNRNPA2B1 and KHSRP, whose expression increases in response to BRCA1 loss. Furthermore, reduction of HNRNPA2B1 treated with siRNA for HNRNPA2B1 induces faster DNA repair. Considering these results, it is assumed that overexpression of HNRNPA2B1 occurring in the early stage of carcinogenesis inhibits DNA-PK activity, resulting in subsequent accumulation of erroneous rejoining of DNA double-strand breaks, causing tumor progression.

According to these genes, the DNA repair response is the predominant process revealed. As expected, this response is associated with a signal leading to growth arrest as well as with factors regulating proliferation and senescence. All these activities were confirmed by the genes PTPN11, SMARCE1, SRRT, SUMO1, and TNFSF10.

Among these genes, TNFSF10/TRAIL induction contributes to cell death in the p53-dependent DNA damage response. Expression of this gene might suggest that the product will first initiate a signal inducing a DNA damage response, which in turn will generate ROS production, leading to an oxidative stress. Concomitantly, protective responses including DNA repair and anti-oxidant activities will be stimulated.

The sustained up-regulation of the genes described below confirmed that the treatment leads to a strong DNA double-strand break response as well as to anti-oxidative effects, which are however elicited by DNA damage signals towards ROS production. It has to be noticed that the remaining genes up-regulated at 3, 9 and 24 hours were neither correlated significantly to "DNA repair" and/or "oxidative stress" nor related to shared functions.

It was therefore important to investigate, by identifying genes up-regulated at 3 hours, how this response is initiated.

Thus, a more drastic selection was applied based on filtering genes whose modulation presents a fold change ≥1.45 in all combined ratio solely at 3 hours.

Among the 65 genes selected according to these criteria, 6 genes, RAD50, SMC6, TDG, THOC2, UPF2 and USP47, were co-cited significantly with "DNA repair", supporting again that this process occurs at an early stage in response to the treatment.

Among the genes up-regulated in response to the treatment specifically at 9 and 24 hours, the induction of SDHD (succinate dehydrogenase complex, subunit D, integral membrane protein) and TFAM (transcription factor A, mitochondrial) was observed. These genes encode proteins involved in mitochondrial DNA repair and mitochondrial biogenesis.

SDHD encodes a member of complex II of the respiratory chain, which is responsible for the oxidation of succinate. The encoded protein is one of two integral membrane proteins anchoring the complex to the matrix side of the mitochondrial inner membrane. Expression of SDHD is regulated positively by GABPA (GA binding protein transcription factor, alpha subunit 60 kDa) which expression was observed at 3 hours.

GABPA encodes one of three GA-binding protein transcription factor subunits which functions as a DNA-binding subunit. Since this subunit shares identity with a subunit encoding the nuclear respiratory factor 2 gene, it is likely involved in activation of cytochrome oxidase expression and nuclear control of mitochondrial function.

Like SDHD, expression of TFAM observed at 9 and 24 hours can be induced by GABPA or by PPARGC1A/PGC-1 (peroxisome proliferator-activated receptor gamma, coactivator 1 alpha).

TFAM encodes a key mitochondrial transcription factor containing two high mobility group motifs. TFAM also functions in mitochondrial DNA replication and repair. Additionally, TFAM can be activated by ATM-dependent phosphorylation of AMPKA. ATM has been reported to phosphorylate the alpha subunit of AMP-activated protein kinase (AMPK), which senses AMP/ATP ratio in cells, and can be activated by upstream kinases. Indeed, upon sensing double-stranded DNA breaks (DSBs), ATM is activated through autophosphorylation and phosphorylates a number of substrates for DNA repair, cell cycle regulation and apoptosis. DNA damage such as (DSBs) has been reported to stimulate mitochondrial biogenesis. As mentioned earlier I this report, the major player in response to DSBs is ATM (ataxia telangiectasia mutated).

Of note, mitochondria have their own genome, which is essential for proper oxidative phosphorylation needed for a large part of ATP production in a cell. Mitochondrial DNA (mtDNA) is highly susceptible to oxidative stress and mtDNA damage leads to mitochondrial dysfunction.

Similarly, induction of MRE11A was observed at 9 and 24 hours. MRE11A (meiotic recombination 11 homolog A) forms a complex with RAD50/NBS1 which acts as a double-strand break sensor for ATM and recruits ATM to broken DNA molecules. Inactive ATM dimers were activated in vitro with DNA in the presence of this complex, leading to phosphorylation of the downstream cellular targets p53 and Chk2 MRE11A encodes a nuclear protein involved in homologous recombination, DNA double-strand break repair and telomere length maintenance.

BRD3 (bromodomain containing 3) was also induced at 9 and 24 hours. It was identified based on its homology to the gene encoding the RING3 protein, a serine/threonine kinase. Bromodomain proteins Brd2 and BRD3 (with the latter induced at 9 and 24 hours) associate preferentially in vivo with hyperacetylated chromatin along the entire lengths of transcribed genes. Brd2- and BRD3-associated chromatin is significantly enriched in H4K5, H4K12, and H3K14 acetylation and contains relatively little dimethylated H3K9. Both Brd2 and BRD3 allowed RNA polymerase II to transcribe through nucleosomes in a defined transcription system.

Associated to this network, another regulator of chromatin encoded by SMARCA2/BRM1 (SWI/SNF related, matrix associated, actin dependent regulator of chromatin, subfamily a, member 2) is induced in response to treatment at 9 and 24 hours. Members of this family have helicase and ATPase activities and are thought to regulate transcription of certain genes by altering the chromatin structure around those genes. The encoded protein is part of the large ATP-dependent chromatin remodeling complex SNF/SWI, which is required for transcriptional activation of genes normally repressed by chromatin. Additionally inactivation of this complex decrease cell survival.

DMTF (cyclin D binding myb-like transcription factor 1) was induced at 9 and 24 hours. It is a transcription factor that contains a cyclin D-binding domain, three central Myb-like repeats, and two flanking acidic transactivation domains at the N- and C-terminal. DMTF is induced by the oncogenic Ras signaling pathway and functions as a tumor suppressor by activating the transcription of ARF and thus the ARF-p53 pathway to arrest cell growth or induce apoptosis. It has been found that DMTF1 and p53 can interact directly in mammalian cells via the carboxyl-terminus of p53 and the DNA-binding domain of DMTF1. Expression of DMTF1 antagonizes ubiquitination of p53 by Mdm2 and promotes nuclear localization of p53. DMTF1-p53 binding significantly increases the level of p53, independent of the DNA-binding activity of DMTF1.

Activation of the tumor suppressor protein p53 is a critical cellular response to various stress stimuli and to inappropriate activity of growth-promoting proteins, such as Myc, Ras, E2F, and beta-catenin. Protein stability and transcriptional activity of p53 are modulated by protein-protein interactions and post-translational modifications, including acetylation.

Another gene, PTMA (prothymosin alpha) induced at 9 and 24 hour following treatment by the test cream is able to stimulate transcription of p53-responsive reporter gene. Consequently, down-regulation of endogenous PTMA by RNA interference approach inhibits transcriptional activity of the p53 tumor suppressor in a reporter gene assay. PTMA is a 12-kDa acidic protein with multiple biological functions. One of its functions is the ability to enhance antioxidant defense system of a cell via its interaction with Keap1 protein. Keap1 is a repressor of NFE2L2/NRF2, a transcription factor responsible for activation of genes that code for defensive proteins. While bound to NFE2L2/NRF2, Keap1 exports NFE2L2/NRF2 from the nucleus to the cytoplasm and, being adaptor protein for ubiquitin ligase, promotes ubiquitination of NRF2 and its subsequent degradation by 26S proteasome. PTMA and NRF2 compete for interaction with Keap1, therefore PTMA is able to liberate NRF2 from the complex formed with Keap1 and hence contributes to NRF2-dependent transcription. Further, PTMA plays a feed-back role in the NFE2L2/NRF2 signaling pathway by mediating the nuclear import of Keap1/Cul3-Rbx1 in order to lower NFE2L2/NRF2 levels in the nucleus, allowing the cell to return to normal conditions. Once in the nucleus, PTMA dissociates from the Keap1/Cul3-Rbx1 complex, allowing NFE2L2/NRF2 to bind to the complex for degradation. Thus, PTMA triggers a tight control of NRF2 activity by either dissociating Keap1 from NRF2 or by degrading NRF2 to switch off the activation of NRF2 downstream gene expression required to maintain accurate homeostasis of the protective activities.

The transcription factor NFE2L2/NRF2 is constitutively expressed in all tissues, although levels may vary among organs, with the key detoxification organs (kidney and liver) exhibiting highest levels. NFE2L2/NRF2 may be further induced by cellular stressors including endogenous reactive-oxygen species or exogenous electrophiles. The NFE2L2/NRF2-signaling pathway mediates multiple avenues of cytoprotection by activating the transcription of more than 200 genes that are crucial in the metabolism of drugs and toxins, protection against oxidative stress and inflammation, as well as playing an integral role in stability of proteins and in the removal of damaged proteins via proteasomal degradation or autophagy. NFE2L2/NRF2 interacts with other important cell regulators such as tumor suppressor protein 53 (p53) and nuclear factor-kappa beta (NF-κB) and through their combined interactions is the guardian of healthspan, protecting against many age-related diseases including cancer and neurodegeneration.

Associated to p53 regulation, it has been found that ZEB1/DELTAEF1 plays a role in the transcriptional regulation of p53 family members during keratinocyte differentiation.

In line with the induction of DNA repair, several repressed genes in response to treatment with the test cream are involved in growth arrest and support the fact that the treatment inhibits proliferation and induce DNA repair. Those repressed genes are listed below.

Among them, IGF2 (insulin-like growth factor 2) was repressed at 3 hours. It is a member of the insulin family of polypeptide growth factors, which are involved in growth and cell proliferation. IGF2 induces expression of KRT19. As a result KRT19 was also repressed at 9 hours in our study. KRT19 encodes a keratin intermediate filament protein responsible for the structural integrity of epithelial cells and are subdivided into cytokeratins and hair keratins. The type I cytokeratins consist of acidic proteins which are arranged in pairs of heterotypic keratin chains. KRT19 is specifically expressed in the periderm, the transiently superficial layer that envelopes the developing epidermis. When overexpressed, IGF2 correlates with the induction of Matrix Metalloproteinase 7 (MMP7) during the hyperproliferation of cells. The repression of IGF2, KRT19 and MMP7 supports the likelihood of reduced cellular hyperproliferation LIF (leukemia inhibitory factor) is known to elicit strong tyrosine phosphorylation and specific DNA-binding activity of STAT3 which is a transcription factor necessary for the G1 to S phase cell cycle transition, thus being association with cell proliferation. Here, LIF was repressed at 3 hours.

Similarly, SERTAD3 has two transcript variants with short mRNA half-lives, and one of the variants is tightly regulated throughout G1 and S phases of the cell cycle. Overexpression of SERTAD3 induces cell transformation in vitro and tumor formation in mice, whereas inhibition of SERTAD3 by small interfering RNA (siRNA) results in a reduction in cell growth rate. Here, SERTAD3 was repressed at 9 and 24 hours S100 calcium binding protein A3 encoded by S100A3 is a member of the S100 family of proteins containing 2 EF-hand calcium-binding motifs. S100A3 are localized in the cytoplasm and/or nucleus of a wide range of cells, and involved in the regulation of a number of cellular processes such as cell cycle progression and differentiation. 5100A3 was repressed at 24 hours.

Like S100A3, TCHH, trichohyalin, encodes for epidermal structural proteins and calcium-binding proteins and both are localized at chromosomal locus 1q21. The locus 1q21 constitutes a gene complex called epidermal differentiation complex. TCHH was repressed at 24 hours.

Finally, transgelin encoded by TAGLN gene is a transformation and shape-change sensitive actin cross-linking/gelling protein found in fibroblasts and smooth muscle. Its expression is down-regulated in many cell lines, which was the case at 3 hours in our study and this down-regulation may be an early and sensitive marker for the onset of transformation.

The present transcriptomic study suggests that the Test Cream stimulates the cutaneous intrinsic defense of the skin (i.e., keratinocytes, fibroblasts etc.) against an oxidative stress and even more strongly against DNA damage. An important upstream factor, ABL2/ARG, was identified which can be considered as a link between these two processes. Indeed, the protective effect is believed to rely on the ability of ABL2/ARG to interact with CAT, to reduce the oxidative defects as well as with RAD51 to stimulate a DNA repair response. This DNA repair response targets predominantly a repair of DNA double strand breaks as illustrated by numerous genes that encode proteins related to this particular process.

The upstream signaling stimulated in response to the test cream is believed to depend on the activation of the ATM (ataxia telangiectasia mutated) pathway, which involved ABL2/ARG and RAD50. Of note, a tight control of the Nrf2 activity to preserve the homeostasis of the response will be ensured by the up-regulated expression of prothymosin alpha (PTMA). In addition, anti-oxidative and DNA repair responses are associated with signals leading to growth arrest to avoid the propagation of unhealthy cells before the repair process is fully achieved.

Protein Expression Results.

Cross-sections from skin explants treated with the Test Cream, Base Cream for 7 days and the untreated explants were subjected to immunostaining for catalase at days 3 and 7. Specifically, explant cross-sections were reacted with the anti-catalase antibody to visualize the presence of catalase.

FIG. 1 is a chart comparing the extent of CAT immunostaining exhibited by the skin explant specimens, with B0 representing untreated explants maintained in survival in BEM medium at 37° C. in a humid, 5%-$CO_2$ atmosphere for 24 hours; ED3 representing explants treated with 1 mg of the Base Cream, 2 times a day for 3 days; PJ3 representing explants treated with 1 mg of the Test Cream, 2 times a day for 3 days; EJ7 representing explants treated with 1 mg of the Base Cream, 2 times a day for 7 days; and PJ7 representing explants treated with 1 mg of the Test Cream, 2 times a day for 7 days.

FIG. 1 demonstrates that the extent of immunostaining in the stratum corneum is the strongest in PJ7, the explants treated with the Test Cream, 2 times a day for 7 days.

Morphological Results.

Cross-sections of control skin explants and skin explants treated with the Test and Base Creams were processed for histological analysis to show the morphology of the layers of skin. The sample sections were stained according to Masson's trichrome, Goldner variant. The microscopic observations of the samples were realized using a Leica DMLB or Olympus BX43 microscope. Pictures were digitized with an Olympus DP72 camera and the Cell^D data storing software. The benefits of the Test Cream on improving the quality of aging skin, and of the various layers or components of the said skin are described and compared to the base cream treated samples and the untreated ones.

The general morphology at Day 0 for all explant cross-sections reveals a stratum corneum that is thick, moderately laminated, moderately keratinized on surface and clearly at its base. The epidermis presents 4 to 5 cellular layers with a good morphology. The relief of the dermal-epidermal junction is clear. The papillary dermis presents thick collagen bundles forming a quite dense network. It is well cellularized. On 3 h, 9 h and 24 h, whatever the treatment, the general morphology is not modified.

On Day 3, the control skin explants and the skin explants treated with the Base Cream exhibited a general morphology that was similar to that observed on Day 0. The skin explants treated with the Test Cream exhibited a clear increase in the epidermal rete ridges.

On Day 7, the control skin explants and the skin explants treated with the Base Cream again exhibited a general morphology that was similar to that observed on Day 0. The skin explants treated with the Test Cream exhibited a moderate increase in the number of cellular layers (6 to 7 layers) with slight densification of the papillary dermis.

Overall, the Test Cream induces a moderate epidermal stimulation characterized by a moderate increase of the epidermal thickness (from 4-5 cellular layers to 6-7 cellular layers). The Test Cream also increases the relief of the epidermal rete ridges and increases the densification of the collagen network in the papillary dermis. In contrast, the control skin explant and the Base Cream explant do not show noteworthy alterations to the skin.

EXAMPLE 3

Protective Effects Against Damage from UV Radiation

The protective effects of the Test Cream on treated skin explants exposed to UV-A and UV-B were studied by observation of the general morphology after staining the skin explants according to Nrf2 immunostaining and thymine dimer immunostaining.

Skin explants were obtained from a 47 year old female donor and incubated for 24 h at 37° C. in a humid 5%-$CO_2$ atmosphere before treatment. On D0, D1, D2, and D5, the Test and Base Creams were topically applied, 1 mg in the morning and 1 mg in the evening) on the surface of the explants and spread with a small spatula.

On D6, the skin explants were either left non-irradiated or irradiated at a dose of 9 J/cm2 UV-A (2 DEM) and 0.3 J/cm2 UV-B (2 DEM) using a Vilbert Lourmat UV simulator RMX 3W. Before irradiation, the explants were cultured in HBSS medium. Unirradiated batches were kept in the dark. After irradiation, all the explants were cultured in BEM. Samples for each explant were taken 6 hours after irradiation to be immunostained.

Nrf2 Immunostaining.

Nrf2 immunostaining was performed on paraffinized sections with the mouse polyclonal anti-human Nrf2 (Santa Cruz ref. Sc-722) at 1/100 for 2 hours at room temperature. Staining was revealed by avidin/biotin amplifier system using Vector's Vectastain Kit and Vector's VIP peroxidase substrate.

Nrf2 is a key transcription factor in the cellular response to oxidative stress. Human Nrf2 has a predicted molecular mass of 66 kDa and it is ubiquitously expressed in a wide range of tissues and cell types. Under oxidative stress, including UV irradiation, Nrf2 is activated by phosphorylation and translocate from the cytoplasm to the nucleus. So far, different cytosolic kinase, including protein kinase C (PKC), phosphatidylinositol 3-kinase (PI3K), mitogen-activated protein kinase (MAPK), and ER-localized pancreatic endoplasmic reticulum kinase (PERK) have been shown to modify Nrf2 and are potentially involved in the dissociation of Nrf2 from its inhibitor, Keap1. Once in the nucleus, Nrf2 binds the DNA at the location of the antioxidant response element (ARE), called also hARE (human antioxidant response element) which is the master regulator of the total antioxidant system.

Figure 2:
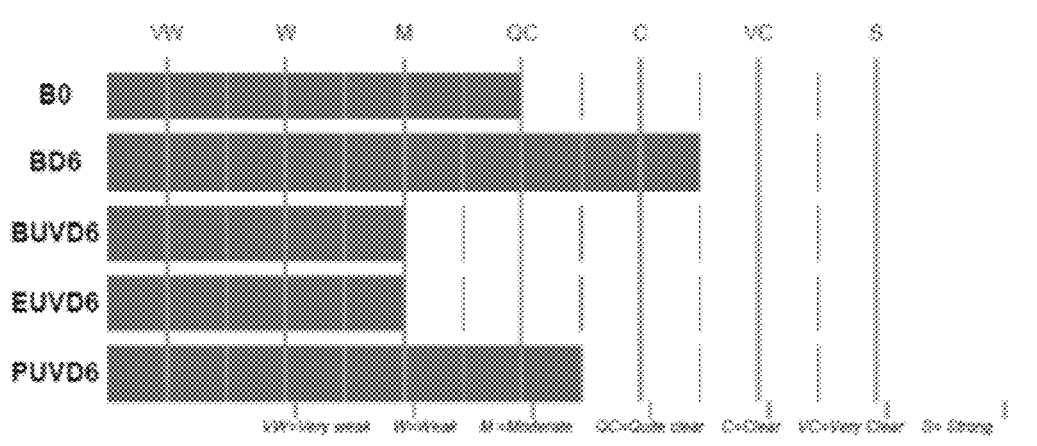
FIG. 2 represents the amount of Nrf2 detected by immunostaining on untreated control skin explant specimens at days 0 and day 6 (B0 and BD6). Skin explant specimens treated for 5 days with a Test Cream (P) or a Base Cream (E) were exposed to UVA-B radiation at day 6 and Nfr2 immunostaining was performed 6 hours after UV exposure on the explants treated with the Test Cream (PUVD6) or the Base Cream (EUVD6).

FIG. 2 is a chart comparing the extent of Nrf2 immunostaining exhibited by the skin explant specimens, with B0 representing untreated explants maintained in survival in BEM medium at 37° C. in a humid, 5%-$CO_2$ atmosphere for 24 hours; BD6 representing untreated explants maintained in survival in BEM medium at 37° C. in a humid, 5%-$CO_2$ atmosphere for 6 days; BUVD6 representing untreated explants maintained in survival in BEM medium at 37° C. in a humid, 5%-$CO_2$ atmosphere for 6 days, exposed to UV irradiation on day 6; EUVD6 representing explants treated with 1 mg of the Base Cream, 2 times a day for 3 days and exposed to UV irradiation on day 6; and PUVD6 explants treated with 1 mg of the Test Cream, 2 times a day for 3 days and exposed to UV irradiation on day 6. All samples were immunostained 6 hours after UV exposure.

There is clear presence of Nrf2 in both untreated skin explants after 24 hours (B0) and more markedly after 6 days (BD6). This is representative of the basal intermittent expression of Nfr2 gene. Following UV irradiation, the untreated explants (BUVD6) and the explants treated with the Base Cream (EUVD6) exhibited a significant decrease in the Nrf2 concentration whereas those treated with the Test Cream (PUVD6) experienced a lesser decrease in Nrf2 when compared to BUVD6 and EUVD6. This suggests that the Test Cream partially inhibits the negative effects of UV-A and UV-B on the epidermis by enhancing the expression of the Nfr2 gene and make more Nfr2 available for translocation and translation of protective enzymes.

Thymine Dimer Immunostaining.

Thymine dimer immunostaining was performed on paraffinized sections with mouse monoclonal anti-human thymine dimers Kamiya (ref. MC-062), Clone KTM53 at 1/1000 for 1 h at room temperature. Staining was revealed by avidin/biotin amplifier system using Vector's Vectastain Kit and Vector's VIP peroxidase substrate. The immunostaining was assessed by microscopial observation and by image analysis using Cell^D software.

Ultraviolet light is absorbed by a double bond in thymine and cytosine bases in DNA. This added energy opens up the bond and allows it to react with a neighboring base. If the neighbor is another thymine or cytosine base, it can form a covalent bond between the two bases. These dimers are awkward and form a stiff kink in the DNA. Thus, the impact of such events are deleterious when the cell needs to replicate its DNA. DNA polymerase has difficulty reading the dimer, since it does not fit smoothly in the active site.

Figure 3:
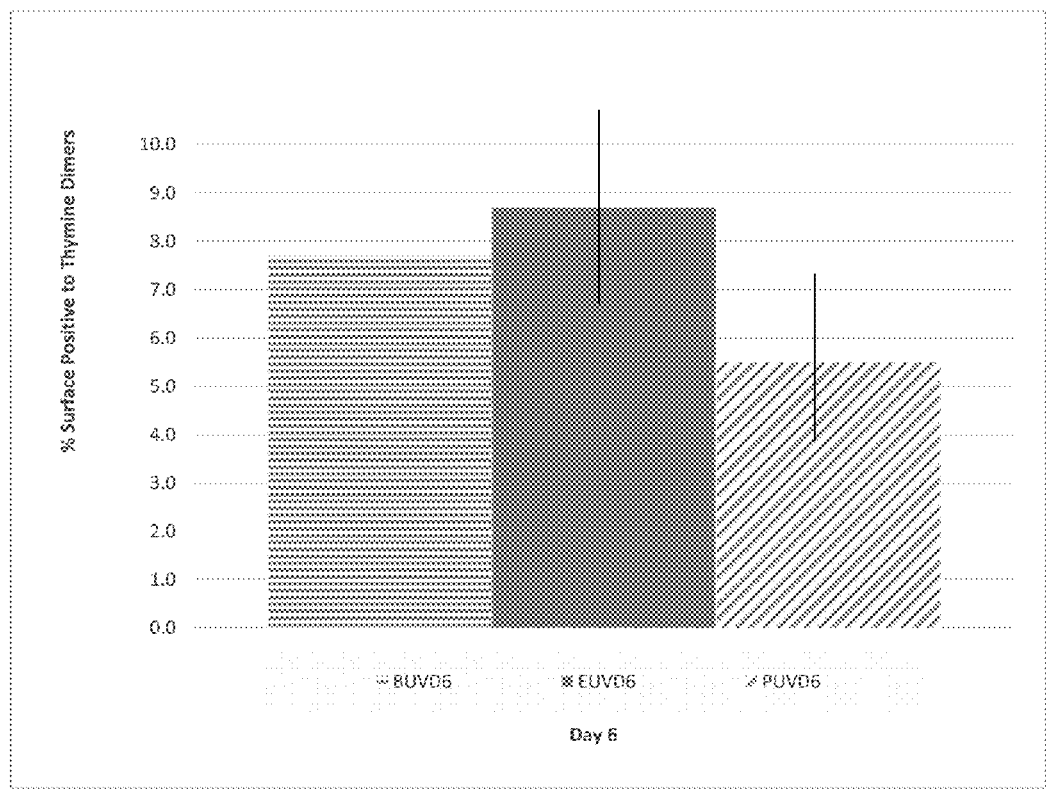
FIG. 3 compares the surface percentage positive for thymine dimers following UV irradiation. BUVD6 refers to untreated skin explants that received UV irradiation at day 6. PUVD6 refers to skin explants treated with the Test Cream for 5 days, exposed UV irradiation on day 6, and analyzed for thymine dimers 6 hours later. EUVD6 refers to skin explants treated with the Base Cream for 5 days, exposed to UV on day 6 and analyzed for thymine dimers 6 hours later.

FIG. 3 is a chart showing the surface percentage positive for thymine dimers. The expression of thymine dimers for the skin explants treated with UV was quantified by image analysis. For these batches, the percentage of surface labeled by thymine dimers in the epidermis is summarized in the table below and FIG. 3.

TABLE

Percentage of Surface Labeled by Thymine Dimers

| | Thymine Dimers | | |
|---|---|---|---|
| | BUVD6 | EUVD6 | PUVD6 |
| Average | 7.7 | 8.7 | 5.5 |
| SD | 1.9 | 2.0 | 2.4 |

On the skin explants irradiated with UV-A and UV-B (BUVD6), 7.7% of the surface was found to be positive to thymine dimer immunostaining. In contrast, on skin explants treated with the Test Cream (PUVD6) and irradiated with UV-A and UV-B, only 5.5% of the surface was found to be positive to thymine dimer immunostaining, showing a 29% decrease in the extent of thymine dimer formation following UV-A and UV-B irradiation. On skin explants treated with the Base Cream (EUVD6), 8.6% of the surface was found to be positive to thymine dimer immunostaining.

The invention described and claimed herein is not to be limited in scope by the specific embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. A composition consisting essentially of:
    an extract of a *Brassica* species containing one or more isothiocyanates, wherein the one or more isothiocyanates is present in the composition in an amount of 500 ppm to 1,500 ppm;
    an extract of a *Camellia* species;
    an extract of *Curcuma longa*;
    an extract of *Piper nigrum*;
    an extract of *Plantago lanceolata* containing plantamajoside, wherein the plantamajoside is present in the composition in an amount of 500 ppm to 1,500 ppm;
    an extract of *Silybum marianum*;
    an extract of *Wasabi japonica*; and
    a humectant, wherein the humectant is selected from at least one of propylene glycol, butylene glycol, or pentylene glycol.

2. The composition of claim 1, wherein the *Brassica* species is selected from at least one of *Brassica juncea, Brassica oleracea italica, Brassica oleracea capitata, Brassica oleracea botrytis*, or *Brassica oleracea acephala*.

3. The composition of claim 1, wherein the one or more isothiocyanates contains sulforaphane.

4. The composition of claim 1, wherein the *Camellia* species is selected from at least one of *Camellia oleifera* or *Camellia sinensis*.

5. The composition of claim 1, wherein the extract of *Curcuma longa* contains one or more curcuminoids.

6. The composition of claim 1, wherein the extract of *Piper nigrum* contains tetrahydropiperine.

7. The composition of claim 1, wherein the humectant is butylene glycol.

* * * * *